United States Patent [19]

Poler

[11] 4,249,272
[45] Feb. 10, 1981

[54] INTRAOCULAR LENS

[76] Inventor: Stanley Poler, 78 E. Second St., New York, N.Y. 10003

[21] Appl. No.: 127,450

[22] Filed: Mar. 5, 1980

Related U.S. Application Data

[63] Continuation-in-part of Ser. No. 57,323, Jul. 13, 1979, which is a continuation-in-part of Ser. No. 9,926, Feb. 6, 1979, abandoned.

[51] Int. Cl.³ .......................... A61F 1/16; A61F 1/24
[52] U.S. Cl. ......................................................... 3/13
[58] Field of Search .......................................... 3/13, 1

[56] References Cited

U.S. PATENT DOCUMENTS

| | | | |
|---|---|---|---|
| 3,925,825 | 12/1975 | Richards et al. | 3/13 |
| 3,975,779 | 8/1976 | Richards et al. | 3/13 |
| 4,056,855 | 11/1977 | Kelman | 3/13 |
| 4,073,014 | 2/1978 | Poler | 3/13 |
| 4,110,848 | 9/1978 | Jensen | 3/13 |
| 4,159,546 | 7/1979 | Shearing | 3/13 |
| 4,174,543 | 11/1979 | Kelman | 3/13 |

FOREIGN PATENT DOCUMENTS 2717706  10/1978  Fed. Rep. of Germany ................ 3/13

*Primary Examiner*—Ronald L. Frinks
*Attorney, Agent, or Firm*—Hopgood, Calimafde, Kalil, Blaustein & Lieberman

[57] ABSTRACT

The invention contemplates improved intraocular-lens structures for use as implants in ophthalmological surgery, the lens being a replacement for a cataract-clouded natural lens, and the replacement being installed through the pupil at the iris as the operative step following removal of the cataracted lens. The lens features adapter structure assembled to an optically finished lens element and including plural angularly spaced stabilizing feet which are formed integrally with the body of the adapter and which are axially offset from the adapter body to permit the stabilizing feet and the adapter body to engage features of the eye within the posterior chamber.

9 Claims, 7 Drawing Figures

INTRAOCULAR LENS

RELATED CASE

This application is a continuation-in-part of my copending application, Ser. No. 057,323, filed July 13, 1979, which copending application is a continuation-in-part of my original application, Ser. No. 009,926, filed Feb. 6, 1979 and now abandoned.

BACKGROUND OF THE INVENTION

This invention relates to structures for making an improved lens implant, as a replacement for a cataract-clouded or otherwise diseased natural lens. The invention represents improvement over structures described in my U.S. Pat. No. 4,122,556 and over my various other patent disclosures referred to in said patent. Reference is therefore made to said patent and disclosures for greater background detail as to structure, and manufacturing and manipulating technique.

Regardless of the structure of an intraocular lens and its mount, relatively great skill is required for installation at or through an iris opening, if post-operative trauma are to be avoided. The likelihood of such trauma is also reduced, to the extent that lens mounting structure imposes least restriction upon normal aperture responses of the iris.

BRIEF STATEMENT OF THE INVENTION

It is an object of the invention to provide improved mounting structure for an intraocular lens.

Another object is to provide such structure lending itself to simplified installation through the iris.

It is a specific object to provide such structure with stabilizing means placing virtually no restriction upon the iris, as compared with prior constructions.

It is another specific object to provide such structure with stabilizing means adapted to provide lens-positioning support within and from the inner wall of the crystalline-lens sac, following invasive surgery to remove cataracted material from the sac.

It is also a specific object to provide such structure which lends itself to posterior implantation in a human eye and which is inherently resistive against such secondary membrane growth (i.e., corpuscular regrowth) as might otherwise obscure or degrade optical performance of the implanted lens.

Still another specific object is to achieve the above objects with structure which is inherently capable of securely and accurately positioning an optically finished glass lens element.

The foregoing and other objects and features of the invention are achieved in illustrative forms of an annular adapter which axially retains itself against both axial sides of the peripheral rim of the lens element to which it is assembled. And plural axially compliant stabilizing feet are provided as radially outward projections from the radially outer edge of the annular body of the adapter. Apertures in the feet enable a suture through all the apertures to temporarily hold all feet in radially retracted position, to facilitate operative insertion of the lens and its adapter via the pupil into the posterior chamber, and into the sac from which cataracted natural lens material has been removed. Upon withdrawal of the suture, the feet are released, to conform to the inner wall of the sac, for stabilized positioning of the lens.

DESCRIPTION OF A PREFERRED EMBODIMENT

Preferred embodiments of the invention are shown in the accompanying drawings, taken in conjunction with ensuing text. In said drawings.

Figure 1:
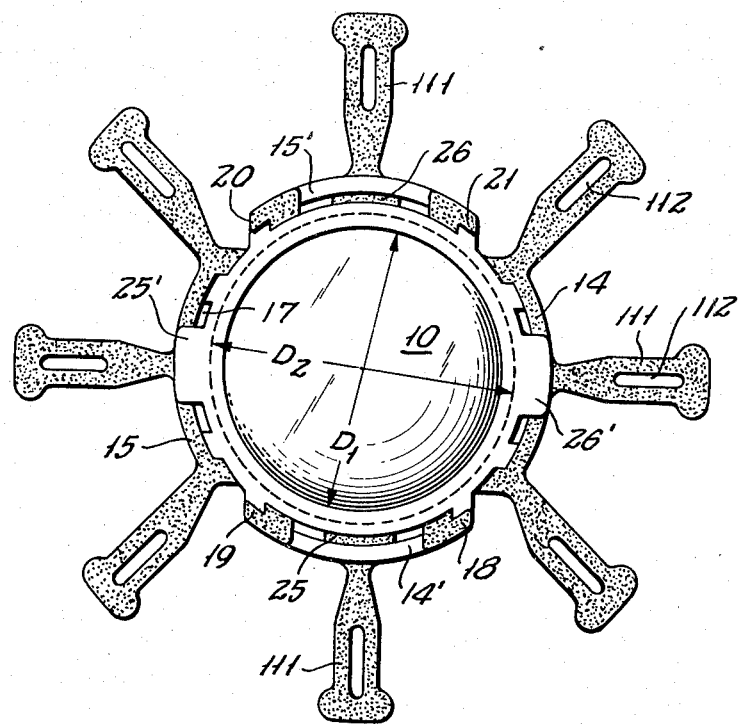
FIG. 1 is a view in elevation of an intraocular lens of the invention, complete with assembled mounting structure.
Figure 2:
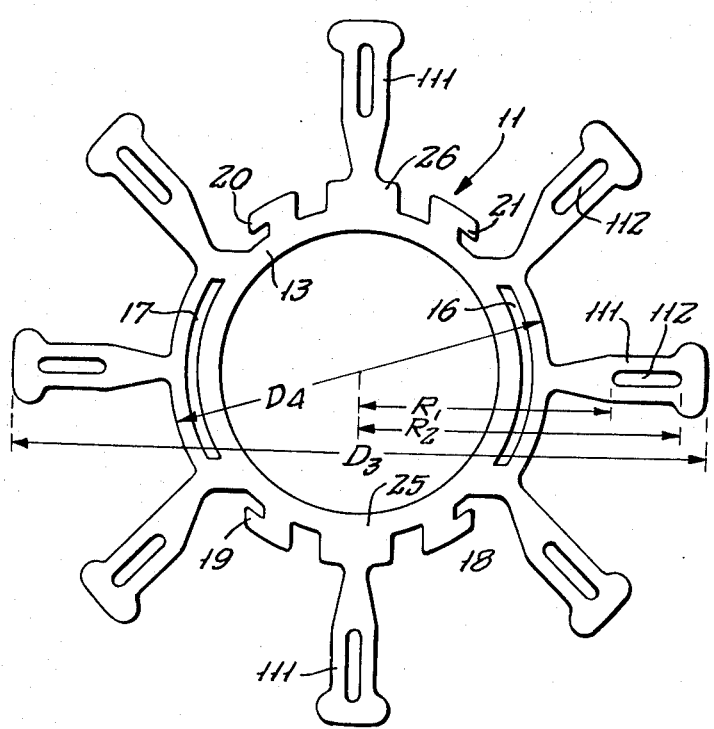
FIGS. 2 and 3 are blank outlines of the respective mounting parts employed in the structure of FIG. 1.
Figure 3:
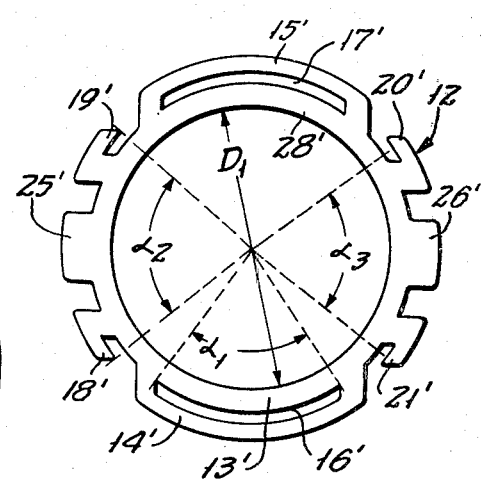

In FIGS. 1 to 3, the invention is shown in application to mounting structure for a finished optical lens element 10 to be surgically implanted in a human eye, relying upon posterior-chamber features for stabilized support of the implant. The mounting structure comprises two parts, a stabilizing-foot part 11 (FIG. 2) and a locking-ring part 12 (FIG. 3), which parts circumferentially continuously overlap opposite axial sides of the rim or peripheral region of lens 10 and which are connected to each other at angularly spaced locations adjacent the lens periphery. Each of these parts, such as the part 11, is characterized by a circumferentially continuous body portion 13 having a circular inner edge of diameter $D_1$ less than the diameter $D_2$ of lens 10 and otherwise in full radial overlap with the lens periphery; because of similarity of certain features of both the part 11 and the part 12, the same identifying numbers as used in FIG. 2 are adopted for corresponding features of FIG. 3, with primed notation. Thus, with the parts 11-12 assembled to each other and to lens element 10 in FIG. 1, the body portion 13 of the part 11 circumferentially continuously laps one side (e.g., the posterior side) of the peripheral region of the lens element, and the body portion 13' of the other part 12 similarly laps the corresponding peripheral region of the opposite side (e.g., the anterior side) of the lens element.

For connected assembly of parts 11-12 to each other, the peripheral regions of both body portions 13-13' are similarly formed with hook and slot formations having diametrically opposite symmetry in diametrically opposite quadrants about the central optical axis. Thus, within a first pair of diametrically opposed quadrants, first and second diametrically symmetrical extensive arcuate tab projections 14-15 are formed with arcuate slots 16-17, of substantial angular extent $\alpha_1$ approaching but less than 90 degrees. And within the remaining or second pair of diametrically opposed quadrants, first and second pairs of diametrically symmetrical hook formations 18-19 and 20-21 project in the circumferentially outward direction with respect to the involved quadrant. The hook formations of member 11 are designed for interlocked engagement in the arcuate-slot formations 16'-17' of member 12, while the hook formations 18'-19' and 20'-21' of member 12 have interlocked engagement in the arcuate-slot formations 16-17 of member 11. To this end, the hook ends in a given quadrant are at an angular spread $\alpha_2$ which exceeds the effective slot width $\alpha_1$, and the closed end of the hook openings in a given quadrant are at an angular spread $\alpha_3$ which is less than the effective slot width $\alpha_1$.

The fully assembled structure is seen in FIG. 1 to involve eight angularly spaced hook-to-slot interlocking engagements around the rim of lens element 10. The hook and slot patterns of the respective parts 11-12 are 90-degrees offset with respect to each other, to enable the described interlocking relation. And the lens element 10 is positively retained by and between circumferentially continuous body surfaces 13-13', with concentric mounting assured by the eight interlocking engagements. Finally, short radially outward integral tab formations 25-26 (25'-26'), between adjacent hook formations 18-19 and 20-21, radially overlap central regions of slotted projections 14'-15' (14-15) to provide additional mutuality of body-member support.

Figure 4:
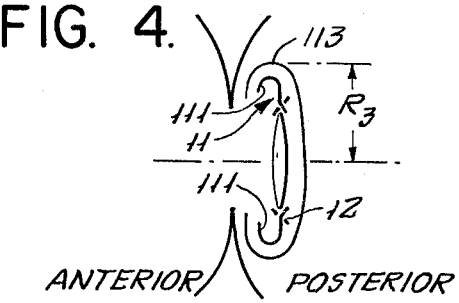
FIGS. 4 and 5 are simplified and somewhat schematic sectional views to show alternative installed implantations of the lens and mount of FIGS. 1 to 3.

The body member 11 is integrally formed with plural radial foot projections 111 which extend from angularly spaced locations on the basic body ring 13, to an overall diametral extent $D_3$, say 10 to 11.5 mm, which exceeds the maximum available mounting diameter within an excavated lens capsule or sac. A slotted region 112 in each of the foot projections 111 renders them more bendable and hence more capable of gentle radially compliant suspension of the mounted lens 10, the radial extent $R_1$-$R_2$ between inner and outer slot limits being selected to be primarily within (i.e., less than) but nevertheless preferably to include the available mounting radius $R_3$ (about 5.5 mm) within the excavated sac 113 (see FIG. 4). In one illustrative operative procedure, a lens 10 mounted by assembled body members 11-12 is transported through the iris opening, using a single releasable filament through all slots, for transient overall size reduction, and using a manipulative tool having releasable engagement with the lens rim. Once past the iris, and suitably oriented, the filament is withdrawn, thereby releasing all feet to restore their FIG. 2 appearance, the feet 111 being then in a radial plane between the iris and the excavated sac 113. The assembly is then further inserted into the sac 113 until feet 111 become deflected and retained by sac-wall engagement, as schematically shown in FIG. 4. The lens 10 is then in a position which as faithfully as possible duplicates the position of the original natural lens, prior to its development of the cataract condition which dictated its removal. It follows that the patient will achieve maximum reinstatement of his original vision capabilities, including a wide angle of peripheral perception.

Figure 5:
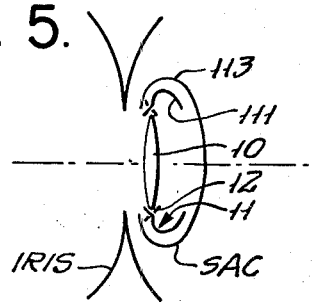

FIG. 5 illustrates that the described structure of FIGS. 1 to 3 may alternatively be used to implant lens 10 more forwardly of the position described for FIG. 4 but nevertheless fully contained within the sac 113, the difference being that the feet 111 compliantly engage the sac wall in the direction rearward of the plane of support of lens 10. To operatively achieve such mounting, a single releasable filament through all slots 112 again draws feet 111 inwardly to develop transient overall size reduction (overall size being then essentially the outer diameter $D_4$ of body 13), but the manipulative tool so engages the lens that the in-drawn feet 111 are first to enter the sac 13. Once lens 10 enters the sac, the filament is withdrawn, to release feet 111 to their FIG. 5 positions of engagement with the sac wall.

Figure 6:
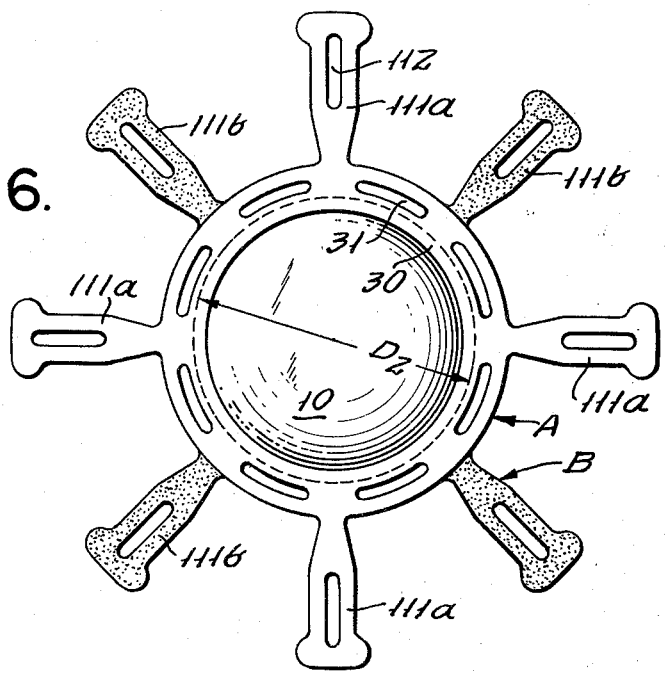
FIGS. 6 and 7 are views similar to FIG. 1 to show modifications.
Figure 7:
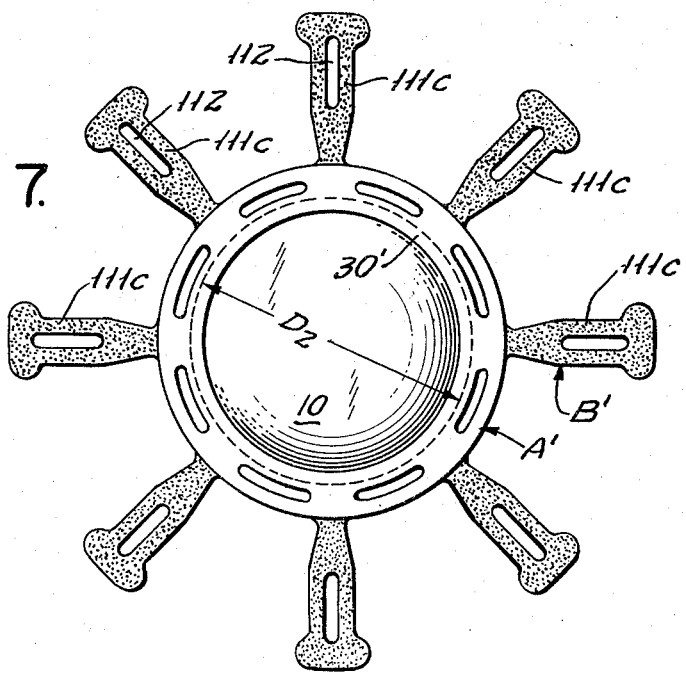

FIGS. 6 and 7 illustrate mounting structure providing sac-engageable feet as in FIG. 1, but without the need for hook-and-slot formations. In the form of FIG. 6, the mount comprises two parts A-B, each having four equally spaced legs 111a-111b as described for the legs 111 of FIG. 2. The parts A-B may be identical and are differentiated in FIG. 6 by shading of part B to the exclusion of part A. Each of parts A and B has a circumferentially continuous annular body 30 which laps a different side of the rim of lens 10, and the bodies 30 are laminated to each other, as by suitable ultrasonic-welding, heat-bonding or cementing techniques, in the region of their registering overlap radially outside the rim of lens 10. The parts A-B are assembled with their bodies 10 in registration but with their feet 111a-111b in angularly staggered interlace. Plural registering spaced arcuate slots 31 outside the lens-rim diameter $D_2$ are preferably located between regions of connection of feet 111a-111b to the registering bodies 30, to facilitate body lamination and enhance lens retention. The resulting product provides the security of a circumferentially continuous laminated body of double thickness, while avoiding the stiffness that would result from laminating feet 111a-111b to each other. In other words, the single-thickness nature of feet 111a-111b renders them weakly compliant, for the ready flexing which is required in the described operative procedures.

The arrangement of FIG. 7 will be recognized for its similarity to FIG. 6, except that the mounting parts A'-B' of FIG. 7 are expressly not duplicates of each other, in that all eight foot formations 111c (being shaded) are integrally formed with the part B', while the part A' is a simple body ring 30'. Registering body slots 31 again enable secure lamination of parts A'-B' and accurate retention of lens 10 by engagement with opposite sides of its rim.

The described body-member configurations and assemblies will be seen to utilize basic two-part lens-mounting structures which are to an extent modular, in that a wide variety of different anterior and posterior suspensions can be provided, to suit the professional preference or decision of the surgeon. Of course, the surgeon will have specified the lens properties appropriate to the ultimate axial location at which he intends to make his implant. In all cases, finish-ground optical quality glass is preferred at lenses 10, generally of 5 mm diameter and 0.3 mm thickness, although if tolerated by the body preformed plastic lenses may be used.

Reference has been made to thin-sheet compliant flexible material for the described mounting structure. This represents my preference, and I indicate my further preference to employ a stable, strong, flexible polyimide, selected for commercial availability and autoclavability. The precise formation of described blank configurations is preferably achieved through photo-lithographic techniques which are described in one or more of the patent disclosures referred to in my said patent. With all presently described forms, thickness of the flexible sheet material is desirably in the range 0.0005 to 0.002 inch, preferably 0.001 inch, at least for the part or parts which embody the compliant feet 111, 111a, 111b, 111c; for a plain ring, as at 12 or A', the 0.002-inch thickness is preferable.

The described structures will be seen to achieve all stated objects and to provide an improved product suited to particular needs, and especially adaptable to quantity production through use of identical lithographically fabricated body blanks on a single sheet. And, the ability to mount the lens independent of relying upon the iris for stabilization, is also expected to materially reduce the likelihood of trauma due to implantation.

While the invention has been described in detail for the preferred forms shown, it will be understood that modifications may be made without departing from the claimed invention.

What is claimed is:

1. As an article of manufacture, an optically finished intraocular lens element having a generally circular periphery about its optical axis, and a mounting adapter for said lens element, said adapter comprising two circumferentially continuous annular body members having a circular inner edge of diameter less than the diameter of said lens element, said body members being adjacent opposite axial sides of the peripheral region of said lens element and being connected to each other within a geometrical annulus radially outside said lens element, and a plurality of angularly spaced lens-positioning feet extending radially outwardly of the periphery of said geometrical annulus and having radially compliant integral connection to one of said body members, said one body member being of compliant flat sheet material and in which all of said feet extend substantially directly radially outwardly to an extent substantially exceeding the maximum inside diameter of the inner wall of a crystalline-lens sac following invasive surgery to remove cataracted material from the sac, each of said feet being sufficiently compliant in its mode of bending from the flat sheet to lightly compliantly adapt to local sac-wall contour at contact therewith.

2. The article of claim 1, in which each of said feet is radially slotted in the region of sac-wall contact, for diminished pressure of compliant contact.

3. The article of claim 1, wherein said feet are slotted over a range of radii which is predominantly less than but nevertheless includes 5.5 mm, whereby said feet may have substantially enhanced radial bending compliance at and near the inner wall diameter of a natural-lens capsule that has had cataracted-lens material removed therefrom.

4. The article of claim 1, in which both said body members are of sheet material, and in which interlocking formations in the sheet material of both body members establish the connection of said body members at a plurality of angularly spaced locations.

5. The article of claim 4, in which for each body member said formations comprise corresponding slot formations within a first pair of diametrically opposed quadrants and corresponding hook formations within the remaining diametrically opposed pair of quadrants, the interconnection of said body members involving the hook formations of one body member engaged to the other body member via the slot formations of said other body member.

6. The article of claim 5, in which the hook formations of said other body member are engaged to said one body member via the slot formations of said one body member.

7. The article of claim 1, in which said body members are connected by lamination of their adjacent surfaces within said geometrical annulus.

8. The article of claim 1, in which both said body members are of compliant sheet material and are duplicates of each other, being connected to each other in such angularly offset relation to each other that the angularly spaced feet of one body member are in angularly interlaced relation with the angularly spaced feet of the other body member.

9. The article of claim 1, in which all of said feet are integrally formed with said one body member, said other body member being annular and radially outwardly limited essentially to the extent of said annulus.

* * * * *